United States Patent [19]

Ogino et al.

[11] Patent Number: 5,428,441
[45] Date of Patent: * Jun. 27, 1995

[54] APPARATUS FOR ANALYZING PARTICLE IMAGES

[75] Inventors: Shinichi Ogino, Nishiku; Tokihiro Kosaka, Kakogawashi, both of Japan

[73] Assignee: Toa Medical Electronics Co., Ltd., Kobe, Japan

[ * ] Notice: The portion of the term of this patent subsequent to Oct. 27, 2009 has been disclaimed.

[21] Appl. No.: 989,062

[22] Filed: Dec. 11, 1992

[30] Foreign Application Priority Data

Dec. 30, 1991 [JP] Japan .................................. 3-359622

[51] Int. Cl.[6] ..................... G01N 33/487; G01N 15/14
[52] U.S. Cl. ..................... 356/73; 250/461.2; 356/39
[58] Field of Search ....................... 356/73, 39, 23, 417, 356/335, 336, 72, 39, 73; 382/6; 250/461.2

[56] References Cited

U.S. PATENT DOCUMENTS

5,159,397 10/1992 Kosaka et al. ........................ 356/73
5,257,085 10/1993 Ulich et al. ............................ 356/73

Primary Examiner—Vincent P. McGraw
Attorney, Agent, or Firm—Jones, Tullar & Cooper

[57] ABSTRACT

An apparatus for analyzing particle images by passing a sample liquid containing blood corpuscles, cells, microorganisms and other particles in a sheath flow, detecting the target particles, and taking the still images thereof efficiently in a simple construction. A sample containing fluorescence dyed particles is passed in a flow cell, the particles in the flow cell are irradiated with light of a specific wavelength, and the fluorescence emitted from the particles is detected by a photo detector to judge whether they are target particles or not in the particle passing judging circuit, and the white images or fluorescent images of the target particles are taken.

8 Claims, 5 Drawing Sheets

APPARATUS FOR ANALYZING PARTICLE IMAGES

BACKGROUND OF THE INVENTION

The present invention relates to an apparatus of simple construction for analyzing particle images for passing a sample liquid containing blood corpuscles, cells, microorganism or other particles in a sheath flow, detecting the target particles, and taking still images thereof efficiently.

The following methods have been hitherto known as the method for analyzing particles in the field of blood analysis or the field of microorganism measurements.

(1) As the method of measuring leukocytes in the field of blood analysis, the method of measuring the fluorescence emitted from dyed cells by a flow cytometer.

(2) In the field of blood analysis, the method of placing a specimen smeared on a slide glass beneath a microscope, moving the stage automatically in the X-, Y- directions, and taking fluorescent images and white light images by a video camera or the like, to thereby achieve a measurement.

(3) In the field of microorganism measurement, the measurement is done by culture inspection requiring various culture media, which took many days until the end of the test. In such a background, various methods have been developed, including the ATP measurement method (see Millon, O., Milsson, L. et al., J. Clin. Microbiol., 18, 521, 1983), impedance method (see Brown, D., Warner, M., Taylor, C. et al., J. Clin. Pathol., 37, 65–69, 1984), enzyme and fluorescence detecting method (see Japanese Laid-Open Patent Sho. 58-116700), and DEFT method combining membrane filter method and fluorescence microscopic method (see G. L. Pattipher, et al., J. Appl. Bacteriol. 53, 323, 1982).

More recently, a "microorganism of a quick measuring apparatus of" is disclosed in Japanese Laid-Open Patent Hei. 3-29837, in which the membrane filter and fluorescence microscope are combined, the sample captured by the filter is dyed with fluorescence, the sample is put on the microscope the sample stage of which automatically moves in the X-, Y-directions, and the cells emitting fluorescence are measured.

However, in method (1), the measured cells can not be recognized visually.

In method (2), the number of cells that can be measured at a time is limited, and the pretreatment of dyeing and smearing is complicated.

Method (3), takes a long time, its precision is not sufficient, and the pretreatment is complicated.

OBJECT AND SUMMARY OF THE INVENTION

It is hence a primary object of the present invention to provide an apparatus for analyzing particle images by passing a sample in a flow cell containing particles dyed with fluorescence, irradiating the particles in the flow cell, for example, cells with light of a specific wavelength, measuring the fluorescence emitted from the cells to judge whether they are target cells or not, and taking the white light images or fluorescent images of the target cells, wherein a small number of particles, such as leukocytes in blood and microorganisms in beer or other beverages may be taken efficiently without overlooking particles.

It is another object of the present invention to provide an apparatus capable of selectively taking and analyzing the images of target particles when a small number of target particles emitting fluorescence are mixed with a large number of particles.

To achieve the above objects, the apparatus of the present invention comprises, for example, an apparatus for analyzing particle images by passing a sample liquid containing particle components or particles in a sheath flow in a flow cell, emitting pulses of light toward the sample flow, and taking the images passing (transmitting) through the particles by image pickup means, comprising:

a flow cell for forming a sample flow, a first light source the detection of particles by always emitting light, an optical filter for obtaining a fluorescence excited light of a specific wavelength from the light emitted from the first light source, a photo detector for detecting the fluorescence emitted from particles by irradiation with the fluorescence excited light, a second light source for taking images by emitting white pulse light, image pickup means irradiated with the white light for taking the particle still images passing (transmitting) through particles, a particle passing judging circuit for detecting the fluorescent signals from the photo detector to judge whether there are target particles or not, and issuing a trigger signal for emitting the second light source when the particles are judged to be the target particles, a dichroic mirror disposed so as to irradiate a region nearly the same as the sample flow region irradiated with the light from the first light source when the light is emitted from the second light source, a further optical filter disposed at a position of passing (transmitting) of the light through the flow cell for cutting off the excited light, a half mirror for dividing the light passing (transmitting) through the optical filter in two parts, into the direction of the photo detector and the direction of the image pickup means, a shutter disposed between the hale mirror and photo the detector, for passing (transmitting) or cutting off the light, so as to be closed while the second light source is emitting light, and a slit disposed between the shutter and the photo detector for forming a narrow sensing region so as to cross the flow of particles in an image pickup region of the image pickup means in the sample flow region.

The sheath flow, meanwhile, refers to a flow of a suspension of particles circumference of which is covered with a laminar sheath liquid in order to align the particles in a row and pass precisely in the middle of the liquid flow.

The invention presents other apparatus for analyzing particle images, in which the light receiving system for particle detection is separated from the imaging system for image pickup, so that the half mirror is not required. That is, apparatus for analyzing particle images by passing a sample liquid containing particle components in a sheath flow in a flow cell, emitting pulses of light to the sample flow, and taking the images passing (transmitting) through the particles by image pickup means, comprises:

a flow cell for forming a sample flow, a first light source for the detection of particles by always emitting light, an optical filter for obtaining fluorescence excited light of a specific wavelength, from the light emitted from the first light source, a photo detector for detecting the fluorescence from particles emitted in a different direction from the light passing (transmitting) direction, a second light source for taking particle images for emitting white pulse light, image pickup means for taking particle still images passing (transmitting) through particles, being irradiated with white light, a particle passing judging circuit for detecting the fluorescent signal from the photo detector to judge whether there are target particles or not, and issuing a trigger signal for emitting the second light source when the particles are judged to be the target particles, a dichroic mirror disposed so as to irradiate a region nearly same as the sample flow region irradiated with the light from the first light source when light is emitted from the second light source, a further optical filter disposed at a position of passing (transmitting) of light through the flow cell, a still further optical filter disposed between the flow cell and the photo detector for cutting off only excited light, a shutter disposed between the optical filter and the photo detector, for passing (transmitting) or cutting off the light, which is controlled to be closed while the second light source is emitting light, and a slit disposed between the shutter and the photo detector so as to form a narrow sensing region to cross the flow of particles in an image pickup region of the image pickup means in the sample flow region, wherein the light receiving system for detecting particles is separated from the imaging system for image pickup.

The present invention presents a different apparatus for analyzing particle images, in which the irradiating system for particle detection is separated from the irradiating system for image pickup, so that the optical filter for cutting off excited light is not needed. More specifically, the apparatus for analyzing particle images by passing a sample flow containing particle components in a sheath flow in a flow cell, emitting pulses of light to the sample flow, and taking the images passing (transmitting) through the particles by image pickup means, comprises:

a flow cell for forming a sample flow, a first light source for detection of particles by always emitting light, an optical filter for obtaining fluorescence excited light of a specific wavelength, from the light emitted from the first light source, a photo detector for detecting the fluorescence emitted from particles by irradiation with the fluorescence excited light, a second light source for taking particle images emitting white pulse light, image pickup means for taking particle still images passing (transmitting) through particles being irradiated with white light, a particle passing judging circuit for detecting the fluorescent signal from the photo detector to judge whether the particles are target particles or not, and issuing a trigger signal for emitting the second light source when judged to be the target particles, a dichroic mirror disposed so as to emit the fluorescence excited light to the sample flow from behind the flow cell, a half mirror for dividing the light passing (transmitting) through the optical filter into two parts, in the direction of the photo detector and the direction of the image pickup means, a shutter disposed between the half mirror and the photo detector, for passing (transmitting) or cutting off the light, as being controlled so as to be closed while the second light source is emitting, and a slit disposed between the shutter and the photo detector so as to form a narrow sensing region so as to cross the flow of particles in an image pickup region of the image pickup means in the sample flow region, wherein the irradiating system for particle detection is separated from the irradiation system for image pickup.

The present invention moreover presents a further different apparatus for analyzing particle images, in which the irradiation system for particle detection, and the light receiving system are individually separated from the irradiation system and imaging system for taking particle images. As a result, the dichroic mirror and half mirror are not needed. More specifically, an apparatus for analyzing particle images by passing a sample liquid containing particles components in a sheath flow in a flow cell, emitting pulses of light to the sample flow, and taking images passing (transmitting) through particles by image pickup means, comprises:

a flow cell for forming a sample flow, a first light source for detection of particles by always emitting light, an optical filter for obtaining fluorescence excited light of a specific wavelength from the light emitted from the first light source, a photo detector for detecting the fluorescence emitted from particles being irradiated with the fluorescence excited light, a second light source for taking images emitting white pulse light, image pickup means for taking particle still images passing (transmitting) through particles being irradiated with the white light, a particle passing judging circuit for detecting the fluorescent signal from the photo detector to judge whether the particles are target particles or not, and issuing a trigger signal for emitting the second light source when the particles are judged to be the target particles, an optical filter disposed between the flow cell and the photo detector so as to cut off the excited light, a shutter disposed between the optical filter and the photo detector, for passing (transmitting) or cutting off the light, being controlled so as to be closed while the second light source is emitting, and a slit disposed between the shutter and the photo detector so as to form a narrow sensing region to cross the flow of particles in an image pickup region of the image pickup means in the sample flow region, wherein the particle detection system and the particle image pickup system are mutually separated from each other, and the two optical axes are intersecting in the sample flow portion.

Instead of placing the shutter before the photo detector, a photo detector with a gate function may be used.

In the apparatus of the present invention, a narrow particle sensing region is formed in the sample flow region so as to cross the flow of particles in the image pickup region of the image pickup means. The excited light from the first light source always irradiates the sample flow, and when the object particles emitting fluorescence pass through the sensing region, their fluorescence is detected by the photo detector, and the pulse light is emitted from the second light source for image pickup. The particle sensing region is formed in a slender form by the slit, crossing inside the image pickup region of the image pickup means. When the second light source emits light, the object particles previously detected are always present in the image pickup region, so that the still images of the particles may be securely taken. If the particle is a non-target particle that does not emit fluorescence when passing through the sensing region, the second light source does not emit light, and image pickup is not effected.

At the time of particle image pickup, since a large quantity of light enters also the photo detector from the second light source, the shutter disposed before the photo detector is closed at the time of image pickup in order to protect the photo detector, so that the light may not reach the photo detector.

DETAILED DESCRIPTION OF THE PREFERRED EMBODIMENTS

Referring now to the drawings, some of the preferred embodiments of the invention are described in detail below.

Figure 1:
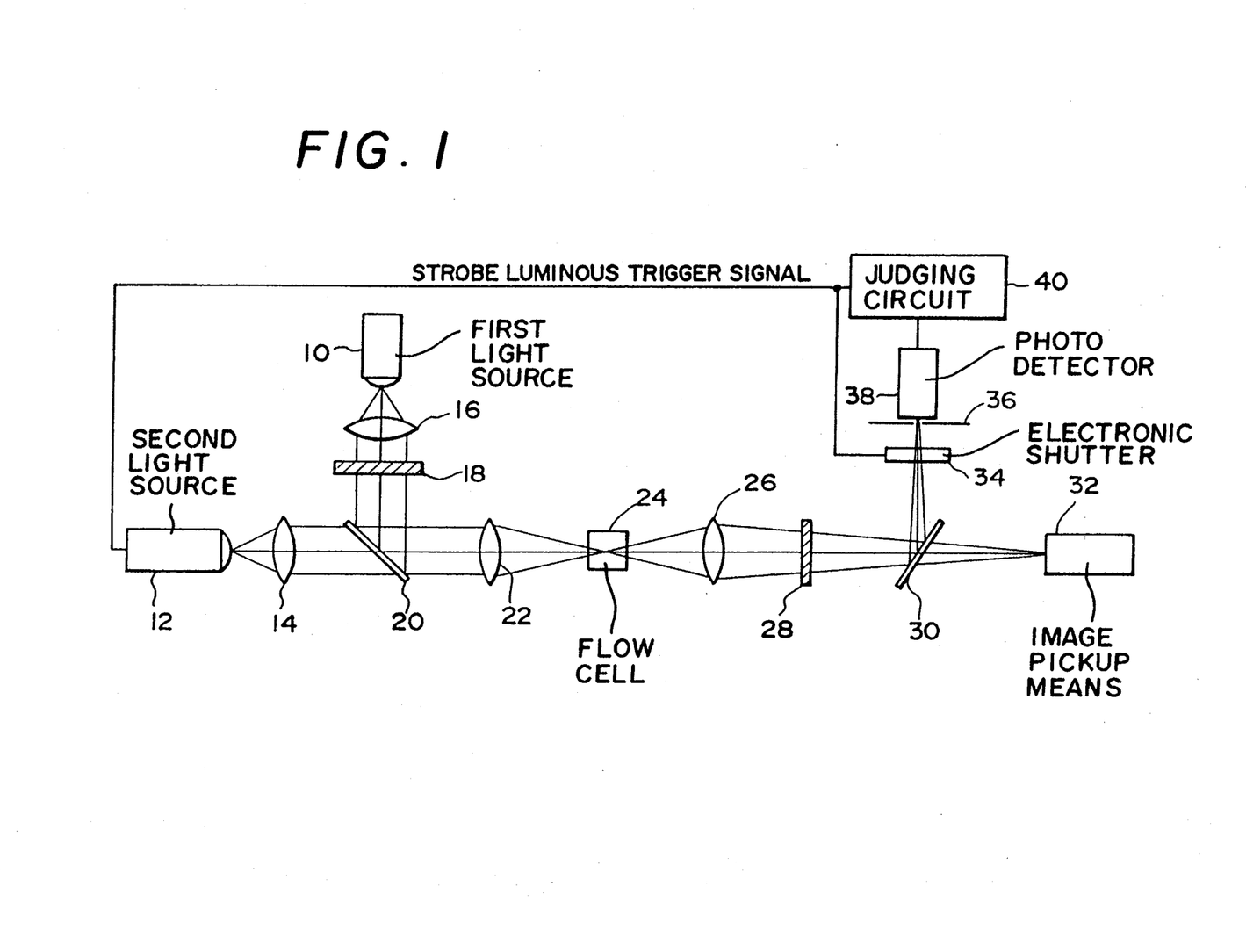
FIG. 1 is a structural explanatory diagram showing an embodiment of the apparatus for analyzing particles images of the present invention.

FIG. 1 is an embodiment of an apparatus for analyzing particle images of the present invention. As the light source, a second light source 12 for white light image pickup (for example, a strobe light source such as a pulse emission type xenon lamp), and a first light source 10 for monitoring the passing of cells (for example, xenon lamp) are used. The first light source 10 is always emitting light.

Figure 2:
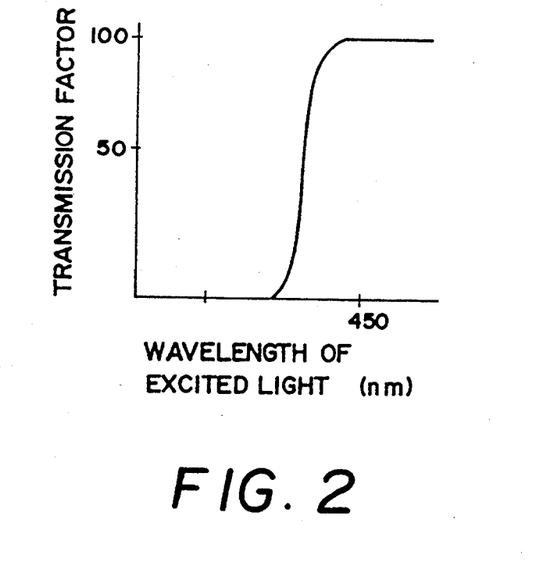
FIG. 2 is an example of characteristic diagram of the dichroic mirror in FIG. 1.

Collimator lenses 14, 16 are intended to regulate the light emitted from the light source 10 or 12 so as to form parallel light. An excited light selective optical filter 18 adjust the wavelength of the light for monitoring passage of cells to the wavelength most appropriate for the object cells and fluorescent dye solution, and the light selective wavelength must be changed depending on the target (for example, when the sample dye agent is fluorescein-diacetate, a filter passing (transmitting) 490 nm is used). The dichroic mirror 20 is intended to irradiate the light of the monitoring light source 10 and the white light image pickup light source 12 toward the flow cell 24, and the light in the wavelength of the monitoring light source 10 is reflected, and the light of the white light image pickup light source 12 is passed (transmitted) (see FIG. 2).

A sample flow containing cells is led into a flow cell 24 composed of a transparent body such as glass or plastic, and a sheath liquid is supplied so as to cover the circumference of the sample flow, thereby forming a sheath flow.

The monitoring light and white light are focused by a condensing lens 22, and are irradiated to the cells flowing in the flow cell 24. The fluorescence or transmitted light emitted from the target cells is focused by an objective lens 26 of a microscope. Of the light focused by the objective lens 26, the light of the excited light wavelength is removed by an excited light cut filter 28, and the fluorescence wavelength and the wavelength in the region for picking up the white light image are led into a subsequent photo detection unit.

A part of the light passing (transmitting) through the filter 28 is reflected by the half mirror 30, and is led into a photo detector 38 (for example, a photo-multiplier tube) for detecting fluorescence.

An electronic shutter 34 placed before the photo detector 38 is intended to cut off the optical path leading to the photo detector 38 when the strobe light source emits light because the element is broken when the strobe light enters the photo detector 38, being emitted at the time of white light image pickup. Instead of the electronic shutter 34, a photo detector incorporating a gate circuit (for example, C1392 of Hamamatsu Photonics) may be used as a substitute for the function of the electronic shutter.

Figure 3:
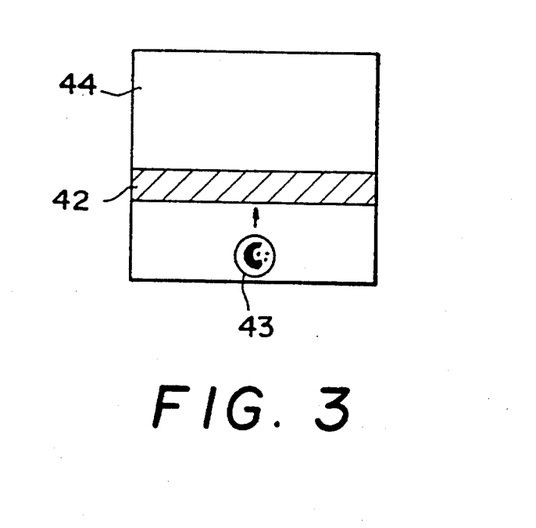
FIG. 3 is an explanatory diagram showing an example of the relationship between image pickup area and slit in the flow cell part shown in FIG. 1.

The slit 36 before the photo detector 38 is intended, as shown in FIG. 3, to limit the fluorescence detecting region in the flow cell part to the sensing region 42 indicated by the shaded area, and its size, that is, the width (in the lateral direction in FIG. 3) should preferably coincide with the width of the image pickup region (viewing field) 44 of the image pickup means (video camera) 32, while the length (in the vertical direction in FIG. 3) should preferably correspond to about 20 $\mu$m in the flow cell. Numeral 43 is a cell. Accordingly, for example, when using a lens of magnifying power 10 as the objective lens 26, the size should be 0.2×1.5 mm, or in the case of a 40 magnifying power lens, 0.8×6 mm. This is because the cell image may not be taken, though a particle is detected, when the particle detecting region is greater than the width of the viewing field region of the video camera.

The particle passing judging circuit 40 which is a strobe control circuit incorporates a cell passing judging circuit and a strobe trigger circuit. In the cell passing judging circuit, detecting the fluorescent signal produced from the photo detector 38, it is judged whether the passing cell is the target cell or not. When judged to be the target cell, in the strobe trigger circuit, a strobe emission (luminous) trigger signal is issued immediately (for example, within 100 $\mu$s in the case of sheath flow velocity of 1 m/s), the second light source (strobe light source) 12 emits strobe light, and the cell image is taken in the video camera by the image pickup means (video camera) 32.

The operation (function) is as follows. The wavelength of the cell passing monitoring light is selected by the excited light selective filter 18, and is always irradiated to the sample in the flow cell 24 by the dichroic mirror 20 and condensing lens 22. When the target cell is not present, the excited light passing through the sensing region 42 in the flow cell corresponding to the slit region before the photo detector 38 is cut off by the excited light cut filter 28 behind the objective lens 26, and does not enter the photo detector 38.

On the other hand, when the target cell passes, the fluorescence emitted from the cell is focused by the objective lens 26, and passes (transmites) through the excited light cut filter 28, and is reflected by the half mirror 30 to enter the photo detector 38. The signal from the photo detector 38 is processed in the particle passing judging circuit 40. In this circuit, the target cell is judged when the input signal intensity is more than a certain value, or the pulse width is more than a certain value, or when both are satisfied, and a trigger signal for emitting the second light source 12 is issued, thereby emitting the second light source 12.

The strobe light passes through the dichroic mirror 20 and condensing lens 22, and is irradiated to the cell in the flow cell 24. The light transmitted through the cell passes through the objective lens 26 and filter 28, and is focused on the image pickup means 32 by transmitting through the half mirror 30, so that the cell image is obtained. What should be noted here is that a part of the light passing through the objective lens 26 at the time of strobe emission is reflected by the half mirror 30 and is directed toward the side of the photo detector 38, and if this light enters the photo detector 38, it destroys the element because the light intensity is high. To avoid this, an electronic shutter 34 is placed before the photo detector 38, and by closing the shutter during strobe emission period, the light is prevented from entering the photo detector 38. Instead of the electronic shutter 34, a photo-multiplier tube with a gate function may be used. Besides, in order that the cell image may not be blurry when taking the still image of the cell, cell movement during the strobe emission period must be controlled under 1 μm, and, for example, if the emission time of the strobe light is 1 μs, the flow velocity of sheath flow must be about 1000 mm/s.

Supposing, for example the diameter of the sample flow in the sheath flow to be 10 μm, only 0.08 μl/s of sample can be analyzed per unit time. Therefore, by forming the sample in a flat flow, when the sample is allowed to flow in the entire viewing field width (for example, 150 μm) of the image pickup means (video camera), the sample amount to be analyzed per unit time may be increased to 1.18 μl/s. The technology for forming a flat flow of sample is disclosed in patent applications (Japanese Patent Applications Hei. 3-210053, Hei. 3-210054).

When a leukocyte cell is the target, for example, by diluting a sample of 5000 leukocytes/μl by 10 times, a measuring sample contains 500 leukocytes/μl. When the sample flow diameter is 10 μm, the sample volume passing the image pickup area in the period of an even-number field (for example, 1/60 sec) is $\pi \times (5 \times 10^{-3})^2 \times 16.7 = 1.3 \times 10^{-3}$ μl. Hence, the mean number of cells passing through the image pickup area in the period of an even-number field is $500 \times 1.3 \times 10^{-3} = 0.65$ cell/field.

Generally, the distribution of particles flowing in a sheath flow conforms to the Poisson's probability distribution, and the probability of imaging of the cell in an arbitrary even-number field period is expressed in the following formula by using the mean interval of particles, which coincides very well with the experiment. In the equation, t is the particle interval.

$$f\beta(t) = \beta e^{-\beta t}$$

More specifically, when the mean of the cells passing through the image pickup area is 0.65/field, the probability of imaging of the cell is 48.0%, and supposing the measuring time to be 45 seconds, 648 cell images are obtained.

Supposing the sample flow to be 150 μm×10μm, similarly, the probability of imaging of the cell is about 100%, and about 1350 cell images are obtained.

When measuring microorganisms, since the number of cells is as small as 100 cells/ml, the sample cannot be measured directly, but by concentrating to about 5000 times by processing the sample by the centrifugal machine or capturing with a membrane filter and diluting, similar results as in leukocyte samples will be obtained.

Next is explained the reason for limiting the fluorescence detecting region by slit 36.

The problem of how many particles flowing in a sheath flow are present in a specific region (for example, the region corresponding to the slit) is presented by the Poisson's probability distribution, and when the particle concentration is low, the probability of the presence of two or more particles is low, but as the concentration becomes higher, it increases. Besides, this probability becomes higher as the area of the region becomes wider. When two or more particles are present in the region (this is called simultaneous passing), the fluorescences emitted from the particles simultaneously enter the photo detector, the sum of the fluorescences emitted from the particles is detected as the signal intensity, and it is possible that something other than the target cell may be mistaken. Besides, when two or more particles emitting fluorescence pass closely, a wider signal than the actual signal is obtained, and something other than the target cell may possibly be mistaken.

Considering from this viewpoint, the shorter side of a rectangular slit should be as short as possible. However, the shorter, the side the less enters the photo detector 38 of the fluorescence emitted from the particles, which means that the cell detection is difficult. Hence, the contradictory problems must both be satisfied. For example, when the concentration of the particles emitting fluorescence is 5000 cells/μl and the region corresponding to the slit in the flow cell is 20 μm×150 μm, the probability of the presence of two or more particles in the slit region is about 1% as estimated from the poisson's probability distribution, and at a lower concentration, the possibility of simultaneous passing is almost nil. Besides, when the region corresponding to the slit is 50 μm×150μm, the probability of two or more particles existing simultaneously is about 5%, and it is known that close passing hardly occurs by using a slit of 20 μm×150μm.

Hence, by limiting the size of the slit to around 20 μm×150μm, the fluorescence entering the photo detector may be considered to be obtained from one particle, so that all target particles passing through the monitor region will be detected.

Figure 4:
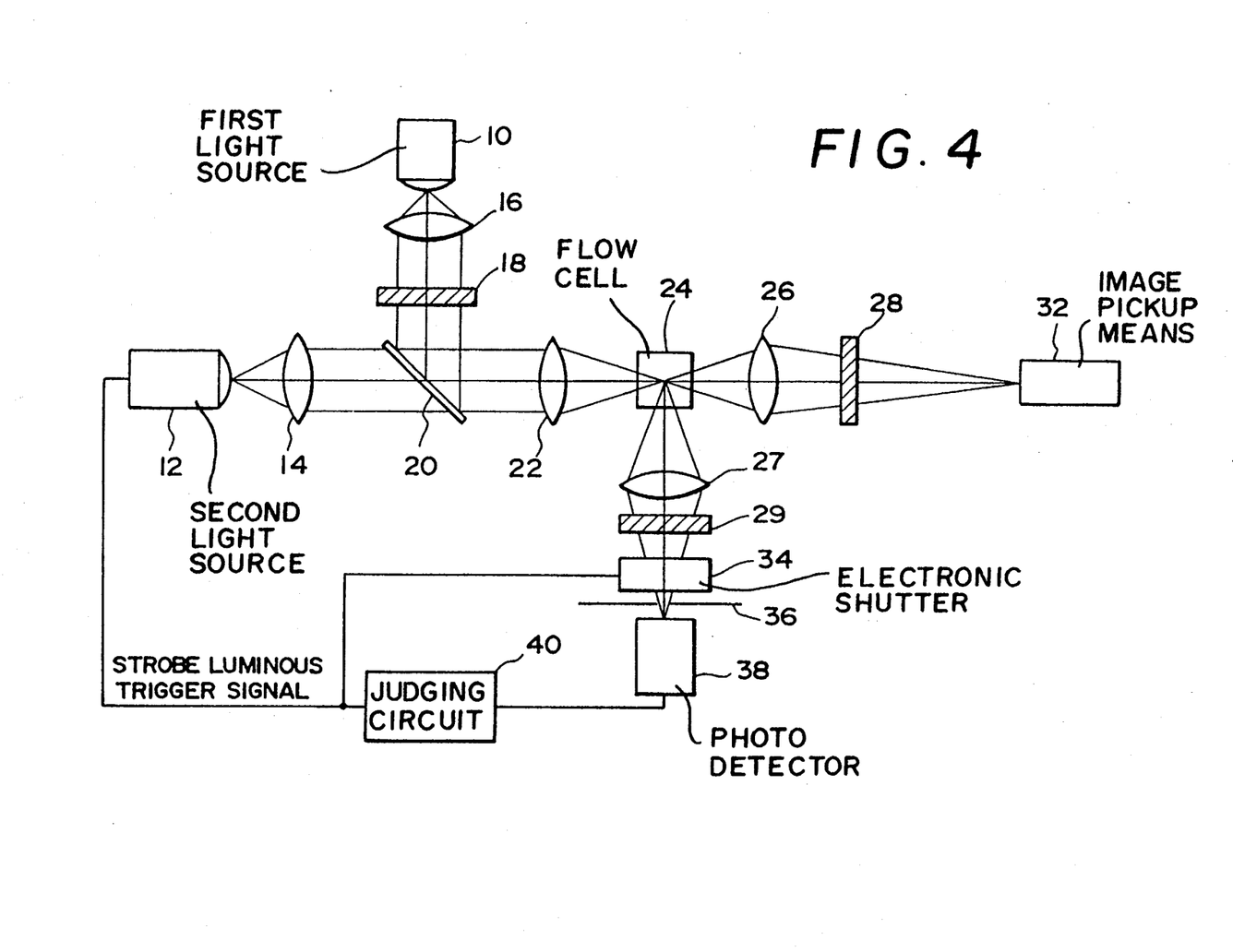
FIG. 4 is a structural explanatory diagram showing another embodiment of the apparatus of the present invention.

FIG. 4 shows another embodiment of the apparatus for analyzing particle images of the present invention. In this embodiment, in order to avoid the defect of the embodiment shown in FIG. 1 that the quantity of light entering the cell detector and video camera is lowered when the light receiving system for cell detection and the light receiving system for image pickup are disposed on the same optical axis because the half mirror 30 must be placed within the system, the optical system for cell detection, that is, the system comprising the objective lens 27, a still further optical filter (excited light cut filter) 29, shutter 34, slit 36 and photo detector 38 is completely isolated from the image pickup system.

In this embodiment, which is different from the above mentioned embodiment in FIG. 1, as a slit 36, a pin hole having a round opening, for example, 150 μm of diameter may be used.

Figure 5:
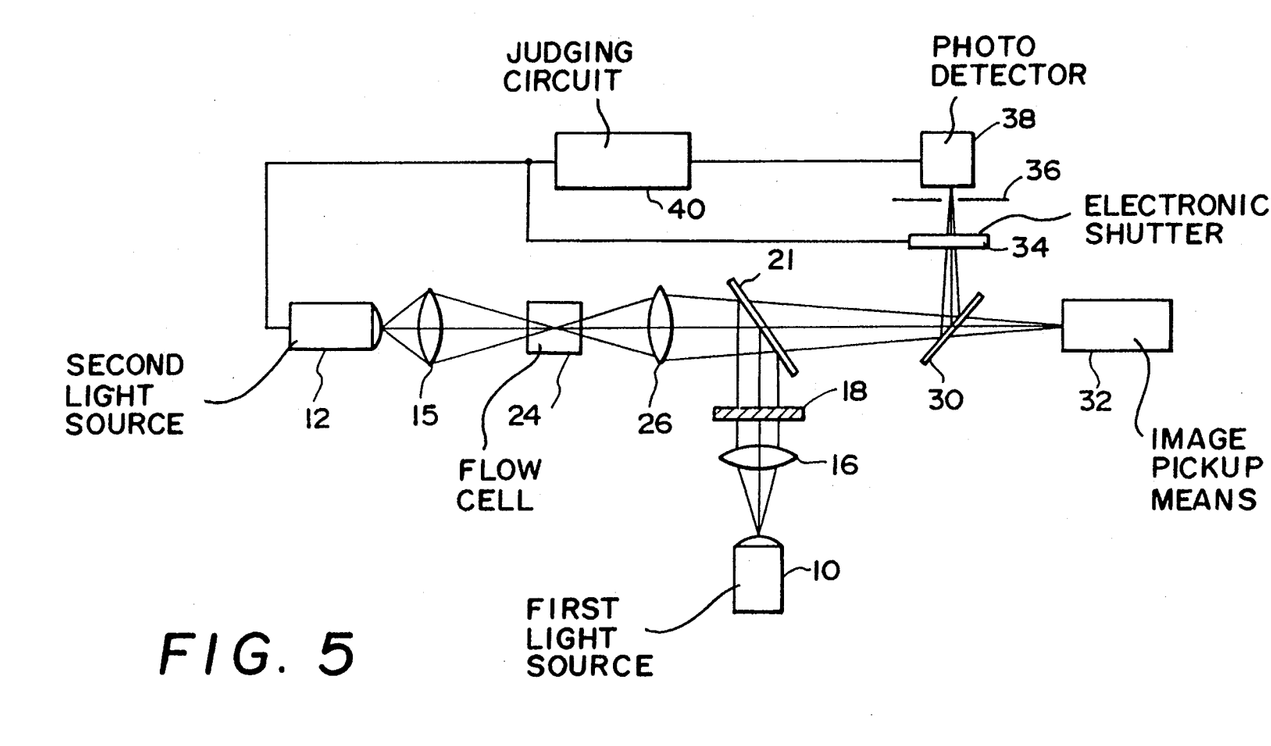
FIG. 5 is a structural explanatory diagram showing a different embodiment of the apparatus of the present invention.

FIG. 5 shows a different embodiment of the apparatus for analyzing particle images of the present invention. In this embodiment, the system for irradiating cell monitoring light in the embodiment in FIG. 1 is disposed at the light receiving side to form the so-called spotlight type. In this case, the excited light cut filter 28 in the embodiment shown in FIG. 1 is not needed, and the construction is simplified.

In the embodiment shown in FIG. 5, the light from the monitoring light source 10 transmits through the flow cell 24, and the quantity reflected to the image pickup means 32 side is small. By setting the characteristic of the dichroic mirror 21 to the characteristic shown in FIG. 2, if the light from the first light source (monitoring light source) 10 is reflected by the flow cell 24 or the cell itself, it is reflected by the dichroic mirror 21, and does not therefore enter the image pickup means (video camera) 32. That is, it works as the excited light cut filter, and therefore it is not necessary to place a cut filter at the image pickup means 32 side.

Figure 6:
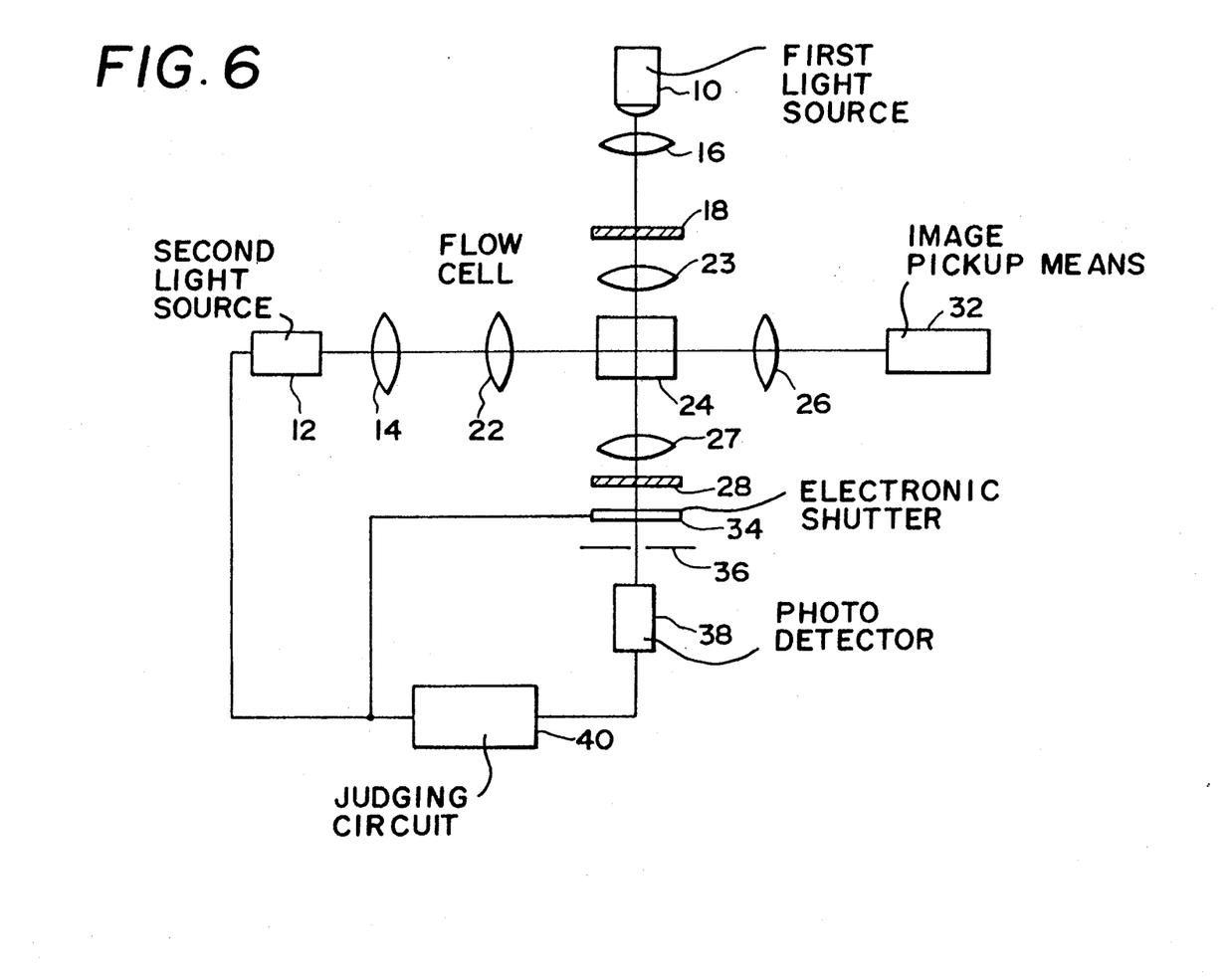
FIG. 6 is a structural explanatory diagram showing a still different embodiment of the apparatus of the present invention.

FIG. 6 shows a further different embodiment of the apparatus for analyzing particle images of the present invention. In this embodiment, the excited light emitted from the monitoring light source 10 may not enter the image pickup means (video camera) 32. Hence, it brings about the following benefits.

(1) It is not necessary to use the optical filter (excited light cut filter) 28 as in the embodiment in FIG. 1 in the white light image pickup system.

(2) If the excited wavelength is light in the white light source wavelength, it has no effect on the white light image. As a result, the degree of freedom of selection of excited light wavelength is enhanced.

(3) The flat flow of sample is detected from the side, and is hence different from the embodiment in FIG. 1. The slit 36 may not be a rectangular slit, and a pin hole of about 150 μm in diameter may be used.

Being thus composed, the present invention brings about the following effects.

(1) Only the target particle out of various particles may be imaged efficiently in a simple structure. In particular, in a sample low in the concentration of the target particles or when a small number of fluorescence emitting particles (target particles) are present in a great number of particles, the images of the target particles may be selectively taken.

(2) By employing the technique of flow imaging, a high processing capacity is obtained, which was impossible in the conventional microscopic measurement.

(3) In the system for fluorescent images, being disposed in the spotlight type, by placing the dichroic mirror after flow cell transmitting, the excited light may be uniformly irradiated to the entire cells. The excited light intensity of about twice the irradiation from one side is obtained.

(4) The target particles can be counted by the signal processing of the particle passing monitor system.

(5) By replacing the optical filter, the excited light wavelength may be set to a desired value, so that wide and general applications may be realized.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. An apparatus for analyzing particle images by passing a sample liquid containing particles in a sheath flow in a flow cell, emitting pulses of light toward the sample flow, and taking the images from the light transmitted by the particles by image pickup means, comprising:

said flow cell for forming a sample flow, a first light source for always emitting light for the detection of particles, an optical filter for obtaining a fluorescence excited light of a specific wavelength from the light emitted from said first light source, a photo detector for detecting the fluorescence emitted from the particles by irradiation with the fluorescence excited light, a second light source for taking particle images by emitting white pulse light, image pickup means irradiated with the white pulse light for taking the particle still images of the transmitting particles, a particle passing judging circuit for detecting the fluorescent signals from said photo detector to judge whether the particles are target particles nor not, and issuing a trigger signal for emitting light from said second light source when the particles are judged to be the target particles, a dichroic mirror disposed so as to irradiate a region nearly similar to the sample flow region irradiated with the light from said first light source when light is emitted from said second light source, a further optical filter disposed to transmit light through said flow cell for cutting off the excited light, a half mirror for dividing the light transmitted by said further optical filter to two parts, in the direction of said photo detector and the direction of said image pickup means, a shutter disposed between said half mirror and said photo detector, for transmitting or cutting off the light, so as to be closed while said second light source is emitting light, and a slit disposed between said shutter and said photo detector for forming a narrow sensing region so as to cross the flow of particles in an image pickup region of said image pickup means in the sample flow region.

2. An apparatus for analyzing particle images of claim 1, wherein a photo detector with a gate function is used instead of said shutter before said photo detector.

3. An apparatus for analyzing particle images by passing a sample liquid containing particles in a sheath flow in a flow cell, emitting pulses of light to the sample flow, and taking the images from the light transmitted by the particles by image pickup means, comprises:

said flow cell for forming a sample flow, a first light source for always emitting light for the detection of particles, an optical filter for obtaining fluorescence excited light of a specific wavelength, from the light emitted from said first light source, a photo detector for detecting the fluorescence from the particles emitted in a different direction from the light transmitting direction, a second light source for taking particle images for emitting white pulse light, image pickup means irradiated with white pulse light, for taking particle still images of the transmitting particles, a particle passing judging circuit for detecting the fluorescent signal from said photo detector to judge whether the particles are target particles or not, and issuing a trigger signal for emitting light from said second light source when the particles are judged to be the target particles, a dichroic mirror disposed so as to irradiate a region nearly similar to the sample flow region irradiated with the light from said first light source when light is emitted from said second light source, a further optical filter disposed to transmit light through said flow cell, a still further optical filter disposed between said flow cell and said photo detector for cutting off only excited light, a shutter disposed between said still further optical filter and said photo detector, for transmitting or cutting off the light, being controlled to be closed while said second light source is emitting light, and a slit disposed between said shutter and said photo detector so as to form a narrow sensing region so as to cross the flow of particles in an image pickup region of said image pickup means in the sample flow region, wherein the light receiving system for detecting particles is separated from the imaging system for image pickup.

4. An apparatus for analyzing particle images of claim 3, wherein a photo detector with a gate function is used instead of said shutter before said photo detector.

5. An apparatus for analyzing particle images by passing a sample flow containing particles in a sheath flow in a flow cell, emitting pulses of light to the sample flow, and taking the images from the light transmitted by the particles by image pickup means, comprises:

said flow cell for forming a sample flow, a first light source for always emitting light for the detection of particles, an optical filter for obtaining fluorescence excited light of a specific wavelength, from the light emitted from said first light source, a photo detector for detecting the fluorescence emitted from the particles by irradiation with the fluorescence excited light, a second light source for taking particle images by emitting white pulse light, image pickup means irradiated with white pulse light for taking particle still images of the transmitting particles, a particle passing judging circuit for detecting the fluorescent signal from said photo detector to judge whether the particles are target particles or not, and issuing a trigger signal for emitting light from said second light source when the particles are judged to be the target particles, a dichroic mirror disposed so as to irradiate the fluorescence excited light to the sample flow from behind said flow cell, a half mirror for dividing the light transmitted by said optical filter into two parts, in the direction of said photo detector and the direction of said image pickup means, a shutter disposed between said half mirror and said photo detector, for transmitting or cutting off the light, being controlled so as to be closed while said second light source is emitting, and a slit disposed between said shutter and said photo detector for forming a narrow sensing region so as to cross the flow of particles in an image pickup region of said image pickup means in the sample flow region, wherein the irradiating system for particle detection is separated from the irradiation system for image pickup.

6. An apparatus for analyzing particle images of claim 5, wherein a photo detector with a gate function is used instead of said shutter before said photo detector.

7. An apparatus for analyzing particle images by passing a sample liquid containing particles in a sheath flow in a flow cell, emitting pulses of light to the sample flow, and taking images from the light transmitted by particles by image pickup means, comprises:

said flow cell for forming a sample flow, a first light source for always emitting light for the detection of particles, an optical filter for obtaining fluorescence excited light of a specific wavelength from the light emitted from said first light source, a photo detector for detecting the fluorescence emitted from the particles as being irradiated with the fluorescence excited light, a second light source for taking particle images by emitting white pulse light, image pickup means irradiated with white pulse light for taking particle still images of the transmitting particles, a particle passing judging circuit for detecting the fluorescent signal from said photo detector to judge whether the particles are target particles or not, and issuing a trigger signal for emitting light from said second light source when the particles are judged to be the target particles, a further optical filter disposed between said flow cell and said photo detector so as to cut off the excited light, a shutter disposed between said further optical filter and said photo detector, for transmitting or cutting off the light, being controlled so as to be closed while said second light source is emitting, and a slit disposed between said shutter and said photo detector so as to form a narrow sensing region so as to cross the flow of particles in an image pickup region of said image pickup means in the sample flow region, wherein the particle detection system and the particle image pickup system are mutually separated from each other, and the two optical axes are intersecting in the sample flow portion.

8. An apparatus for analyzing particle images of claim 7, wherein a photo detector with a gate function is used instead of said shutter before said photo detector.

* * * * *

UNITED STATES PATENT AND TRADEMARK OFFICE
CERTIFICATE OF CORRECTION

PATENT NO. : 5,428,441
DATED : June 27, 1995
INVENTOR(S) : Shinichi Ogino et al

It is certified that error appears in the above-indentified patent and that said Letters Patent is hereby corrected as shown below:

Claim 3, column 11, line 2, "comprises" should be --comprising--.

Claim 5, column 11, line 50, "comprises" should be --comprising--.

Claim 7, column 12, line 28, "comprises" should be --comprising--.

Signed and Sealed this

Nineteenth Day of September, 1995

Attest:

BRUCE LEHMAN

*Attesting Officer*       *Commissioner of Patents and Trademarks*